US009870622B1

(12) United States Patent
Lu et al.

(10) Patent No.: US 9,870,622 B1
(45) Date of Patent: Jan. 16, 2018

(54) SYSTEMS AND METHODS FOR ANALYZING A MOTION BASED ON IMAGES

(71) Applicant: Dyaco International, Inc., Taipei (TW)

(72) Inventors: Tung-Wu Lu, Taipei (TW); Hsuan-Lun Lu, Taipei (TW); Cheng-Kai Lin, Taipei (TW); Hao Chiang, Taipei (TW)

(73) Assignee: DYACO INTERNATIONAL, INC., Taipei (TW)

( * ) Notice: Subject to any disclaimer, the term of this patent is extended or adjusted under 35 U.S.C. 154(b) by 0 days.

(21) Appl. No.: 15/214,375

(22) Filed: Jul. 19, 2016

Related U.S. Application Data

(60) Provisional application No. 62/363,804, filed on Jul. 18, 2016.

(51) Int. Cl.
*G06K 9/00* (2006.01)
*G06T 7/20* (2017.01)

(52) U.S. Cl.
CPC .. *G06T 7/2046* (2013.01); *G06T 2207/10016* (2013.01); *G06T 2207/20148* (2013.01); *G06T 2207/30004* (2013.01); *G06T 2207/30196* (2013.01); *G06T 2207/30221* (2013.01)

(58) Field of Classification Search
CPC ......... G06T 7/2046; G06T 2207/20148; G06T 2207/10016; G06T 2207/3004; G06T 2207/30221; G06T 2207/30196
USPC ........................................ 382/103, 104, 154
See application file for complete search history.

(56) References Cited

U.S. PATENT DOCUMENTS

| 9,001,132 B1 * | 4/2015 | Wooley | G09G 5/00 345/474 |
| 9,589,207 B2 * | 3/2017 | Holohan | G06K 9/00342 |
| 2009/0232353 A1 * | 9/2009 | Sundaresan | G06K 9/00342 382/103 |
| 2011/0228976 A1 * | 9/2011 | Fitzgibbon | G06K 9/00335 382/103 |
| 2012/0159290 A1 * | 6/2012 | Pulsipher | G06K 9/00369 714/819 |
| 2015/0130841 A1 * | 5/2015 | Kohli | G06F 19/321 345/633 |

* cited by examiner

*Primary Examiner* — Tom Y Lu
(74) *Attorney, Agent, or Firm* — Finnegan, Henderson, Farabow, Garrett & Dunner LLP

(57) ABSTRACT

A method for determining posture-related information of a subject using the subject's image is provided. The method comprises: determining, from a first image, first positions of a first pair of joints and a first body segment length of a first body segment associated with the first pair of joints; determining, from a second image, second positions of a second pair of joints and a second body segment length of a second body segment associated with the second pair of joints; determining, based on an algorithm that reduces a difference between the first and second body segment lengths, whether the first and second pairs of joints correspond to a pair of joints; If the first and second pairs of joints are determined to correspond to a pair of joints, determining, based on the second positions, information of a posture of the subject; and providing an indication regarding the information.

40 Claims, 9 Drawing Sheets

First image

| Joint Identifier | X | Y | Z |
| --- | --- | --- | --- |
| A | 0.6 | 0.6 | 0.6 |
| B | 0.8 | 0.8 | 0.8 |
| C | 1.0 | 0.9 | 0.9 |

220

| Body Segment | Length | Mid-point | | | Direction | | |
| --- | --- | --- | --- | --- | --- | --- | --- |
| | | X | Y | Z | X | Y | Z |
| A-B | 0.34 | 0.7 | 0.7 | 0.7 | +0.2 | +0.2 | +0.2 |
| B-C | 0.24 | 0.9 | 0.85 | 0.85 | +0.2 | +0.1 | +0.1 |

| Second Image | | | |
|---|---|---|---|
| Joint identifier | X | Y | Z |
| D | 0.7 | 0.7 | 0.7 |
| E | 0.9 | 0.5 | 0.5 |
| F | 1.1 | 0.6 | 0.6 |

270

| Body Segment | Length | Mid-point | | | Direction | | |
|---|---|---|---|---|---|---|---|
| | | X | Y | Z | X | Y | Z |
| D-E | 0.34 | 0.8 | 0.6 | 0.6 | +0.2 | -0.2 | -0.2 |
| E-F | 0.24 | 1 | 0.55 | 0.55 | +0.2 | +0.1 | +0.1 |

FIG. 2D

SYSTEMS AND METHODS FOR ANALYZING A MOTION BASED ON IMAGES

RELATED APPLICATIONS

This application claims priority to U.S. Provisional Patent Application No. 62/363,804, filed Jul. 18, 2016, the contents of which are hereby incorporated by reference in their entirety.

TECHNICAL FIELD

This disclosure generally relates to motion analysis, and more specifically relates to systems and methods for determining and analyzing a motion of a subject based on images.

BACKGROUND

Motion analysis is an important part of the discipline of biomechanics, and can be associated with various applications such as, for example, balance assessment, force sensing measurement, sports science training, physio analysis, and fitness equipment operation, etc. Motion analysis is typically performed based on images, in which a system captures a sequence of images of a subject (e.g., a human being) when the subject is engaged in a specific motion. The system can then determine, based on the sequence of images, the positions of various body segments of the subject at a given time. Based on the positions information, the system can then determine a motion and/or a posture of the subject at that time.

Current technologies provide various ways of performing image-based motion analysis. One approach is by tracking a motion of markers emitted by the subject. For example, the subject can wear a garment that includes a number of markers. The markers can be passive reflector (e.g., with VICON™ system) or active emitter of visible light or infra-red light (e.g., with PhaseSpace™ system). The system can then use a plurality of cameras to capture, from different angles, a sequence of images of the markers when the subject is in a motion. Based on the sequence of images, as well as the relative positions between each camera and the subject, the system can determine the motion of the subject by tracking the motion of the markers as reflected by images of the markers included in the sequence of images.

Another approach is by projecting a pattern of markers on the subject and then tracking the subject's motion based on images of the reflected patterns. For example, Microsoft's Kinect™ system projects an infra-red pattern on a subject and obtains a sequence of images of the reflected infra-red patterns from the subject. Based on the images of the reflected infra-red patterns, the system then generates depth images of the subject. The system can then map a portion of the depth images of the subject to one or more body parts of the subject, and then track a motion of the depth images portions mapped to the body parts within the sequence of images. Based on the tracked motion of these depth images portions (and the associated body parts), the system can then determine a motion of the subject.

There are disadvantages for both approaches. With the VICON™ system, the subject will be required to wear a garment of light emitters, and multiple cameras may be required to track a motion of the markers in a three-dimensional space. The additional hardware requirements substantially limit the locations and applications for which the VICON™ system is deployed. For example, the VICON™ system is typically not suitable for use at home or in an environment with limited space.

On the other hand, the Kinect™ system has a much lower hardware requirement (e.g., only an infra-red emitter and a depth camera), and is suitable for use in an environment with limited space (e.g., at home). The accuracy of the motion analysis performed by the Kinect™ system, however, is typically limited, and is not suitable for applications that demand high accuracy of motion analysis.

SUMMARY

Consistent with embodiments of this disclosure, a method for determining posture-related information of a subject using the subject's image is provided. The method comprises: receiving a first image of a subject in a first posture; determining, from the first image, first positions of a first pair of joints; determining, from the first positions, a first body segment length of a first body segment associated with the first pair of joints; receiving a second image of the subject in a second posture; determining, from the second image, second positions of a second pair of joints; determining, from the second positions, a second body segment length of a second body segment associated with the second pair of joints; determining, based on a relationship between the first and second body segment lengths, whether the first and second pairs of joints correspond to a pair of joints of the subject; If the first and second pairs of joints are determined to correspond to a pair of joints of the subject, determining, based on the second positions, information of a posture of the subject; and providing an indication regarding the information of a posture of the subject.

Embodiments of the present disclosure also provide a system for determining posture-related information of a subject using the subject's image. The system comprises: a memory that stores a set of instructions; and a hardware processor configured to execute the set of instructions to: receive a first image of a subject in a first posture; determine, from the first image, first positions of a first pair of joints; determine, from the first positions, a first body segment length of a first body segment associated with the first pair of joints; receive a second image of the subject in a second posture; determine, from the second image, second positions of a second pair of joints; determine, from the second positions, a second body segment length of a second body segment associated with the second pair of joints; determine, based on a relationship between the first and second body segment lengths, whether the first and second pairs of joints correspond to a pair of joints of the subject; If the first and second pairs of joints are determined to correspond to a pair of joints of the subject, determine, based on the second positions, information of a posture of the subject; and provide an indication regarding information associated with the posture of the subject.

Embodiments of the present disclosure also provide a non-transitory computer readable medium storing instructions that are executable by one or more processors to cause the one or more processors to execute the aforementioned method of determining posture-related information of a subject using the subject's image.

It is to be understood that both the foregoing general description and the following detailed description are exemplary and explanatory only and are not restrictive of the embodiments of the present disclosure, as claimed.

BRIEF DESCRIPTION OF THE DRAWINGS

The accompanying drawings, which are incorporated in and constitute a part of this specification, illustrate embodiments of the present disclosure and, together with the description, serve to explain the embodiments. In the drawings:

FIGS. 2A-D are diagrams illustrating exemplary data generated by the exemplary system of FIG. 1 for motion analysis, consistent with embodiments of the present disclosure.

DETAILED DESCRIPTION

Figure 1:
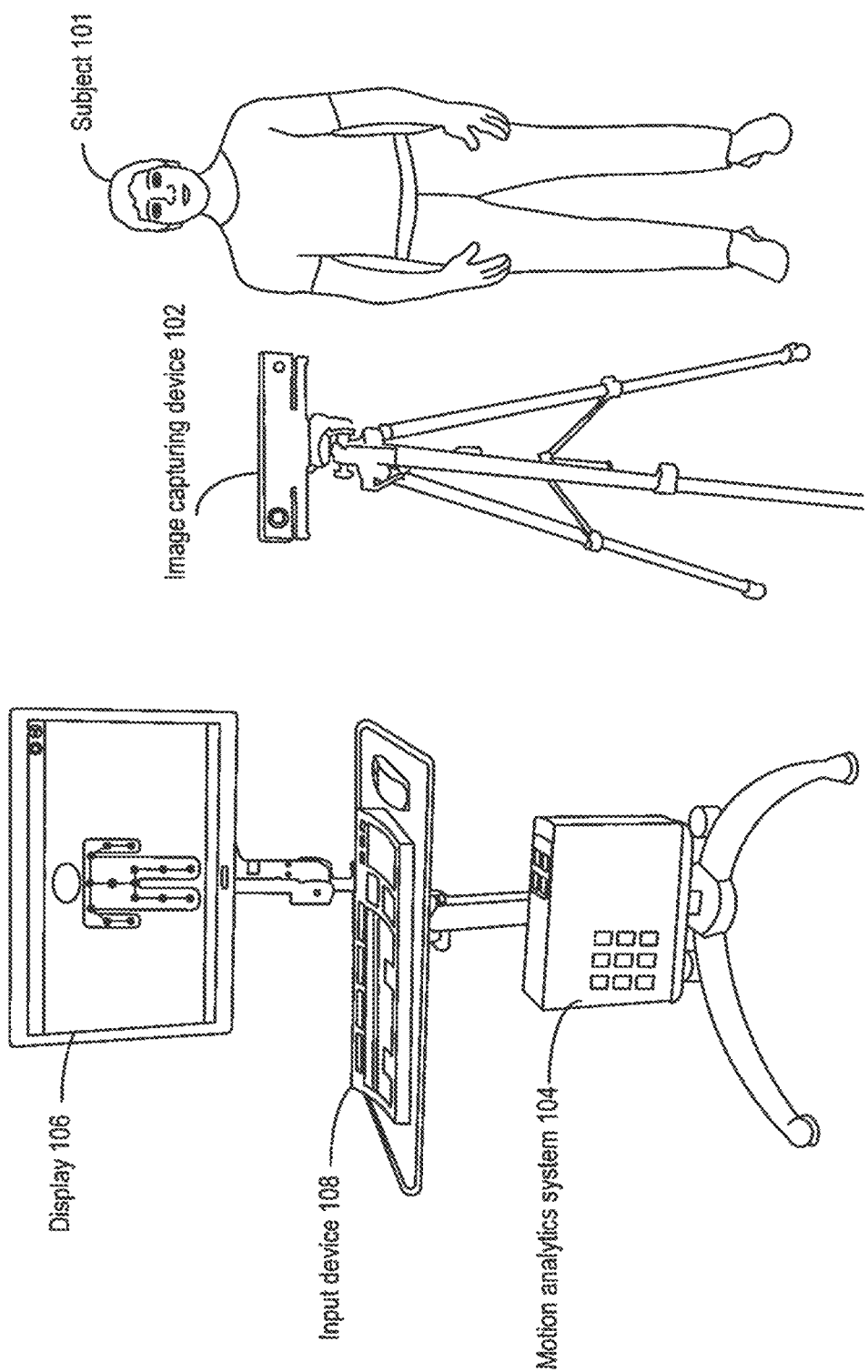
FIG. 1 is an exemplary system for image-based motion analysis, consistent with embodiments of the present disclosure.

Reference will now be made in detail to the disclosed embodiments, examples of which are illustrated in the accompanying drawings. The same reference numbers are used throughout the drawings to refer to the same or like parts.

These and other objects, features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be understood, however, that the drawing(s) are for the purpose of illustration and description only and are not intended as a definition of the limits of the invention. As used in the specification and in the claims, the singular form of "a", "an", and "the" include plural referents unless the context clearly dictates otherwise.

Embodiments of the present disclosure provide a system for determining posture-related information of a subject using the subject's image. The system comprises: a memory that stores a set of instructions; and a hardware processor configured to execute the set of instructions to: receive a first image of a subject in a first posture; determine, from the first image, first positions of a first pair of joints; determine, from the first positions, a first body segment length of a first body segment associated with the first pair of joints; receive a second image of the subject in a second posture; determine, from the second image, second positions of a second pair of joints; determine, from the second positions, a second body segment length of a second body segment associated with the second pair of joints; determine, based on a relationship between the first and second body segment lengths, whether the first and second pairs of joints correspond to a pair of joints of the subject; If the first and second pairs of joints are determined to correspond to a pair of joints of the subject, determine, based on the second positions, information of a posture of the subject; and provide an indication regarding information associated with the posture of the subject.

With embodiments of the present disclosure, a system can identify from a first image of the subject when the subject is in a first posture, first positions of at least two joints associated with the at least one body segment, and a body segment length of the at least one body segment. The system can also identify from a second image of the subject second positions of the at least two joints based on at least the body segment length. The system can then determine a second posture of the subject based on the second positions of the at least two joints. Since the system takes into account at least the prior-determined body segment length in determining a new position of the joints associated with the body segment, the accuracy of tracking the joints positions as the subject changes postures, as well as the accuracy of determining the new posture of the subject, can be improved.

FIG. 1 is a block diagram illustrating an exemplary system 100 for image-based motion analysis, consistent with embodiments of the present disclosure. As shown in FIG. 1, system 100 includes an image capturing device 102 and a motion analytics system 104. Optionally, system 100 may also include a display 106 and an input device 108. System 100 can be used to capture one or more images of subject 101, and then perform image-based motion analysis of subject 101.

In some embodiments, image capturing device 102 includes one or more cameras configured to capture one or more images of subject 101. The cameras can include, for example, a red-green-blue (RGB) camera, an infra-red (IR) camera, a time-of-flight (TOF) camera, etc., all of which configured to capture signals (e.g., visible light, IR, or any kind of signal) reflected off subject 101 to generate an image of the subject. If image capturing device 102 includes an IR camera or a TOF camera, image capturing device 102 may also include a signal emitter device (e.g., an IR emitter, an RF emitter, etc.) configured to project a signal onto subject 101 to generate the reflected signals. Both IR camera and TOF camera can provide three-dimensional location information of subject 101. Further, the subject may also wear a garment that includes one or more signal emitters, and the cameras may capture, as part of the image, the signals emitted by the signal emitters.

Based on the image data captured by image capturing device 102, motion analytics system 104 can determine a motion, or at least a posture at a particular time, of subject 101. To determine the posture, analytics system 104 can determine, from the image data, the locations (e.g., midpoints) of one or more body segments, as well as the orientations of the body segments, of the subject. The system can then determine a posture of the subject based on the orientations of the body segments.

Figure 2A:
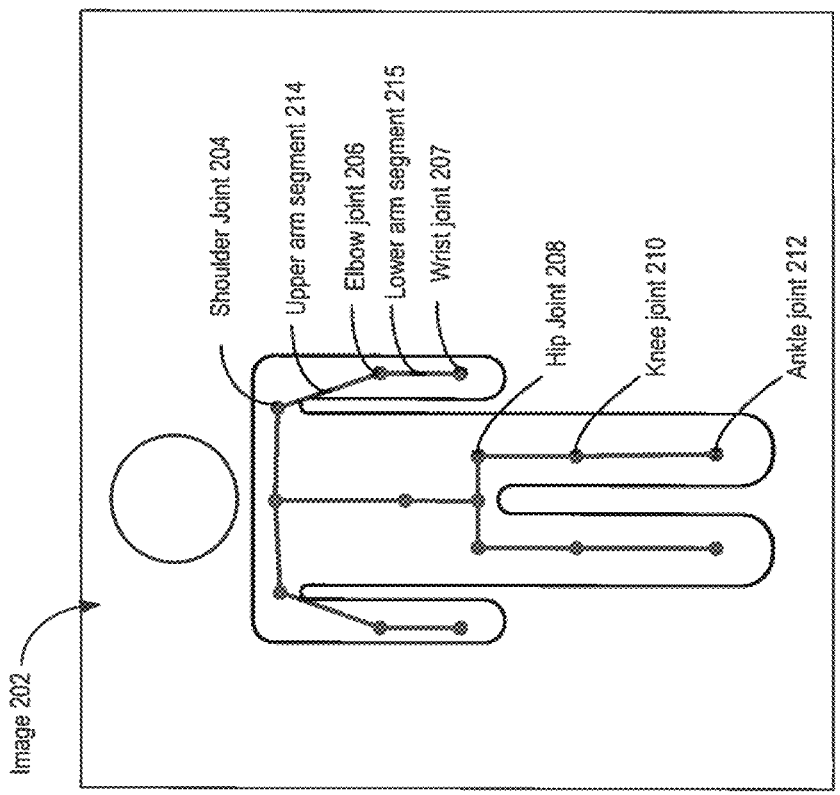

In some embodiments, analytics system 104 can determine a location of a body segment by first identifying, from the image data, one or more joints, and the locations of the joints. Reference is now made to FIGS. 2A-2D, which illustrate exemplary data generated by system 100 for motion analysis. FIG. 2A illustrates an outline of subject 101 in an image 202. Image 202 can be captured by image capturing device 102 when subject 101 is in a first posture (e.g., standing). From image 202 (or a set of images including image 202), motion analytics system 104 can identify a number of joints of subject 101 including, for example, shoulder joint 204, elbow joint 206, wrist joint 207, hip joint 208, knee joint 210, and ankle joint 212. A pair of joints can also be associated with a body segment. For example, shoulder joint 204 and elbow joint 206 can be associated with an upper arm segment 214, while elbow joint 206 and wrist joint 207 can be associated with a lower arm segment 215.

There are various ways by which analytics system 104 can identify the joints from image 202. For example, analytics system 104 can compare a portion of image 202 against a database of known images of joints, to determine whether the portion of image 202 corresponds to a joint. The known images of joints may include data representing a certain pattern of signals (IR, visible light, etc.) reflected from a joint. The known images of joints may also include data representing a certain pattern of signals emitted by signal emitters on a garment that covers the joint. If image capturing device 102 captures both an RGB image and an IR (or TOF) image, analytics system 104 can also align the RGB image with the IR image, and detect certain features from the RGB image to facilitate the identification of the joints.

After determining a certain portion of the IR image includes an image of a joint, motion analytics system 104 can then determine a three-dimensional location of the joint. For example, motion analytics system 104 can determine the coordinates of the joint on a two-dimensional plane (e.g., defined by an x-axis and a y-axis which are orthogonal to each other) based on a location of the joint's image with respect to the boundaries of the IR image. Further, if the IR image includes a depth image, motion analytics system 104 can also determine, based on the depth information provided in the depth image, the coordinate on the third dimension (e.g., along a z-axis that is orthogonal to both of the x-axis and the y-axis).

After identifying the joints from image 202, and determining the three-dimensional locations of these joints, analytics system 104 can determine one or more body segments defined by a pair of the identified joints. The determination of the body segments can be based on, for example, determining a distance between a pair of joints and comparing the distance against a threshold. The threshold can be set based on, for example, an average body segment length (e.g., an average arm segment length, an average leg segment length, etc.), and based on the location of the joints. If the distance exceeds the threshold, analytics system 104 may determine that a pair of joints is not associated with a body segment; instead, each of the pair of joints probably is associated with different body segments. As an illustrative example, analytics system 104 may determine that a distance between shoulder joint 204 and hip joint 208 exceeds an average arm segment length and may determine that shoulder joint 204 and hip joint 208 are not associated with the same body segment, but are associated with different body segments.

After identifying the joints and the associated body segments, motion analytics system 104 may also determine the locations and orientations of the body segments. A location of a body segment can be represented by, for example, a mid-point between the pair of joints associated with the body segment. Further, the orientation of the body segments can also be represented in the form of a direction vector determined from, for example, the relative locations of the pair of joints. For example, assuming that the three-dimensional coordinates of the pair of joints are $(x_1, y_1, z_1)$ and $(x_2, y_2, z_2)$, the three-dimensional coordinates of the mid-point location of the body segment associated with the pair of joints can be determined based on the following equation:

$$(x_{mid}, y_{mid}, z_{mid}) = \left(\frac{x_1+x_2}{2}, \frac{y_1+y_2}{2}, \frac{z_1+z_2}{2}\right)$$

Further, the orientation of the body segment can also be represented by the following direction vector:

$$(\hat{x}, \hat{y}, \hat{z}) = (x_1-x_2)\hat{i} + (y_1-y_2)\hat{j} + (z_1-z_2)\hat{k}$$

Here, $\hat{i}$, $\hat{j}$, and $\hat{k}$ are unit vectors, each of which represents a vector associated with a predefined direction in a space. For example, each of these unit vectors can be orthogonal to each other, and that each of these unit vectors is aligned to a dimension in a three-dimensional space. For example, $\hat{i}$ can be aligned with the x-axis, $\hat{j}$ can be aligned with the y-axis, and $\hat{k}$ can be aligned with the z-axis.

Tables 220 of FIG. 2C illustrates examples of joints locations, each of which is associated with a joint identifier. For example, as represented in the first image, the three-dimensional coordinates of joints A, B, and C are, respectively, (0.6, 0.6, 0.6), (0.8, 0.8, 0.8), and (1.0, 0.9, 0.9). Moreover, table 230 of FIG. 2C illustrates examples of body segment lengths, locations (mid-points), and orientations of body segments associated with pairs of joints A, B, and C. For example, body segment A-B, which is associated with joints A and B, has a body segment length of 0.34, a mid-point coordinates of (0.7, 0.7, 0.7), and a direction vector of $0.2\hat{i}+0.2\hat{j}+0.2\hat{k}$. The data can be stored at, for example, a database coupled with motion analytics system 104 (not shown in FIG. 1).

In some embodiments, the data in tables 220 and 230 can be generated from a set of first images. For example, motion analytics system 104 may receive a set of first images of subject 101 at the first posture, and then determine the values for the locations of joints A, B, and C, and body segment lengths, locations, and directions of body segments A-B and B-C for each of the set of first images. Motion analytics system 104 can then determine an average for each of the joints locations, body segments lengths, locations, and directions across the set of first images.

Figure 2B:
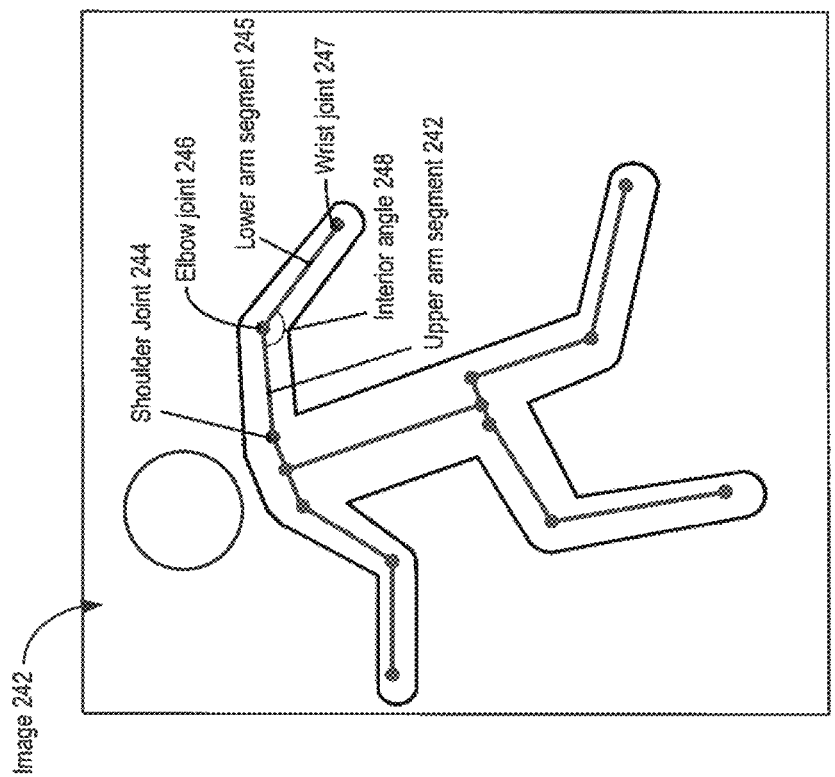

Besides capturing image 202 of the subject when the subject is in a first posture, image capturing device 102 can also capture a second image (or a set of second images) of the subject when the subject is in a second posture. The capturing of the second image can occur before or after the first image. FIG. 2B illustrates an outline of subject 101 in an image 242, when the subject is in a second posture (e.g., running). Motion analytics system 104 can determine, from image 242 (or a set of images including image 242), the second posture of subject 101. The determination of the second posture can include identifying, from image 242, the locations of the joints and the associated body segments, and determining the relative orientations of the body segments. Motion analytics system 104 can identify the joints from the second image based on the techniques described above (e.g., by comparing portions of image 242 against a database of images associated with joints), and determine the three-dimensional locations of the joints based on the image data. The lengths of the body segments associated with these joints, as well as their mid-point locations and orientations, can also be calculated based on the three-dimensional locations of the joints as discussed above.

Tables 260 of FIG. 2D illustrates examples of joints locations, each of which is associated with a joint identifier. For example, as represented in the second image, the three-dimensional coordinates of joints D, E, and F are, respectively, (0.7, 0.7, 0.7), (0.9, 0.5, 0.5), and (1.1, 0.6, 0.6). Moreover, table 270 of FIG. 2D illustrates examples of body segment lengths, locations (mid-points), and orientations of body segments associated with pairs of joints D, E, and F. For example, body segment D-E, which is associated with joints D and E, has a body segment length of 0.34, a mid-point coordinates of (0.8, 0.6, 0.6), and a direction vector of $0.2\hat{i}-0.2\hat{j}-0.2\hat{k}$. The data can be stored at, for example, a database coupled with motion analytics system 104 (not shown in FIG. 1).

After identifying the joints from the second image, motion analytics system 104 can determine which pair of joints determined in the first image and which pair of joints determined in the same image are associated with the same pair of joints of the subject. By associating the joints across different images, the system can track a motion of the joints as reflected by images of the joints.

One way to associate the joints identified in different images (e.g., between images 202 and 242) is by determining a distance between a pair of joints in image 242, and then comparing the distance against a body segment length determined from image 202. Because the corresponding pairs of joints identified in the images represent the same pairs of joints, and are associated with the same body segment, the distance between that corresponding pairs of joints, which reflect the length of the same body segment, should be equal (or substantially equal) to the segment length. In one example, the initial association may consider the two as substantially equal if they are within approximately 5% to 30% of each other. But this range can vary and can be narrower or broader depending on various considerations, such as the accuracy required, the quality of the images, the data available, design choices, etc.

As an illustrative example, motion analytics system 104 may determine whether shoulder joint 244 of image 242 corresponds to shoulder joint 204 of image 202, and whether elbow joint 246 of image 242 corresponds to elbow joint 206 of image 202. Motion analytics system 104 may select joint 244 and joint 204 (and joint 246 with joint 206) for determining whether they represent the same joint based on, for example, a determination that these joints are on the same side of the body. Motion analytics system 104 can determine a length of an upper arm segment 242 (e.g., based on a distance between shoulder joint 244 and elbow joint 246), and compare that against the length of upper arm segment 214 from image 202 to determine a difference. Motion analytics system 104 can then determine a value based on the difference (e.g., a square of the difference, an absolute value of the difference, etc.). If the value is below a difference threshold, motion analytics system 104 can determine that shoulder joint 244 of image 242 corresponds to shoulder joint 204 of image 202, and that elbow joint 246 of image 242 corresponds to elbow joint 206 of image 242.

In some embodiments, motion analytics system 104 may also consider other joints (and other associated body segment lengths) when determining whether two pairs of joints correspond to the same pair of joints of the subject. For example, motion analytics system 104 may determine a set of corresponding joint pairs that, collectively, minimize the differences between the body segment lengths determined from the second image (e.g., image 242) and the body segment lengths determined from the first image (e.g., image 202), according to the equation below:

$$\min f(SL_i) = (SL_i - SL_i^*)^2$$

Here, $SL_i$ can refer to a body segment length determined from the second image, $SL_i^*$ can refer to a body segment determined from the first image, and $f(SL_i)$ represents a function that generates a value based on a square of difference between $SL_i$ and $SL_i^*$. Motion analytics system 104 can apply an optimization algorithm, such as sequential quadratic programming (SQP), the Newton method, or other algorithms, to determine a mapping between the joints represented in the first image and the joints represented in the second image that collectively minimize the output of $f(SL_i)$, and minimize the difference between the corresponding body segments determined from different images. As an illustrative example, the system can determine a set of corresponding joint pairs that minimize an output value of the following summation function:

$$f(SL_0, SL_1, \ldots SL_n) = \sum_{i=0}^{n} (SL_i - SL_i^*)^2$$

In some embodiments, each term $(SL_i - SL_i^*)^2$ can also be scaled by a weight in the summation function.

In some embodiments, motion analytics system 104 may also consider other factors in determining the mapping of the joints across images. For example, motion analytics system 104 may determine, for a particular mapping of the joints, the body segments associated with the joints form a certain angle. If that angle exceeds an angle threshold determined based on known maximum angle of a joint structure, motion analytics system 104 may determine that the mapping is invalid. As an illustrative example, assume that based on a particular mapping of the joints, motion analytics system 104 determines that the upper arm segment 242 and lower arm segment 245 represented in image 242 forms an interior angle 248. If interior angle 248 is determined to exceed 180 degrees, which is the maximum angle allowed by an elbow joint, motion analytics system 104 can determine that the body segment identified as upper arm segment 242 in image 242 is not really an upper arm segment, and/or that the body segment identified as lower arm segment 245 is not really a lower arm segment. Accordingly, motion analytics system 104 can also determine that the particular mapping corresponding to the identification of upper arm segment 242 and lower arm segment 245 from image 242 is to be discarded. As a result, analytics system 104 can select a different mapping for further analysis.

Based on the mapping relationship between the joints represented in different images, motion analytics system 104 can then track a motion (or change in locations and/or orientations) of the body segments. For example, referring to FIGS. 2C and 2D, motion analytics system 104 may determine that body segment D-E of FIG. 2D is associated with body segment A-B of FIG. 2C, and that body segment E-F of FIG. 2D is associated with body segment B-C of FIG. 2C. Accordingly, motion analytics system 104 may also determine that the mid-point and direction information of table 270 reflect a second posture involving the left upper and lower arm segments of the subject.

With embodiments of the present disclosure, since the system takes into account at least the prior-determined body segment length in determining a new position of the joints associated with the body segment, the accuracy of tracking the joints positions as the subject changes postures, as well as the accuracy of determining the new posture of the subject, can be improved. As discussed above, there are various applications for tracking a motion of a subject. Such applications can include, for example, balance assessment, force sensing measurement, sports science training, physio analysis, and fitness equipment operation, etc. With more accurate motion tracking analysis, the effectiveness of these applications can be improved, and user experiences can be improved as well.

Figure 3:
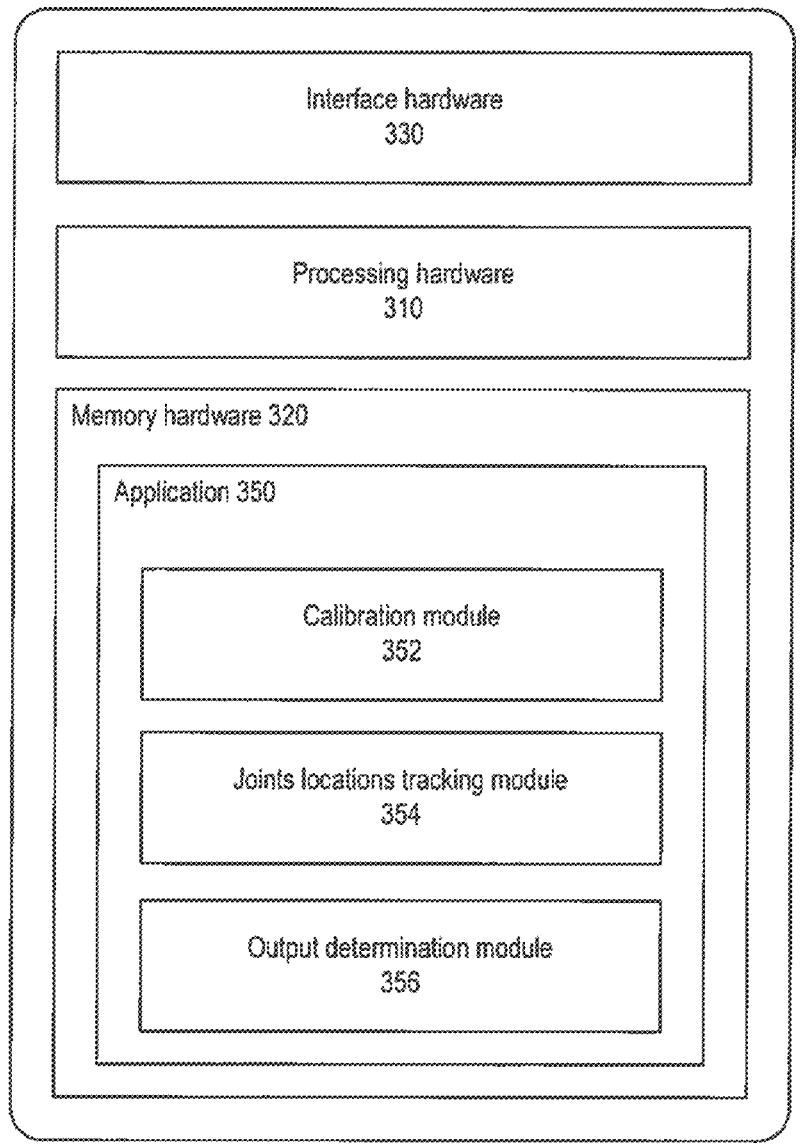
FIG. 3 is a block diagram illustrating an exemplary system for image-based motion analysis, consistent with embodiments of the present disclosure.

FIG. 3 depicts an exemplary system 300, which can be configured as motion analytics system 104 of FIG. 1. System 300 may include processing hardware 310, memory hardware 320, and interface hardware 330.

Processing hardware 310 may include one or more known processing devices, such as a microprocessor, a microcontroller, etc. that are programmable to execute a set of instructions. Memory hardware 320 may include one or more storage devices configured to store instructions used by processing hardware 310 to perform functions related to the embodiments of the present disclosure. For example, memory hardware 320 may store software instructions, such as application 350, that can be executed by processing hardware 310 to perform operations. The embodiments of the present disclosure are not limited to separate programs or computers configured to perform dedicated tasks.

Interface hardware 330 may include interfaces to I/O devices. For example, the I/O devices may include output devices such as a display, a speaker, etc., while input devices may include a camera, a keyboard, etc. Interface hardware 330 may also include a network interface, which may include a wireless connection interface under various protocols (e.g., Wi-Fi, Bluetooth®, cellular connection, etc.), wired connection (e.g., Ethernet), etc. The network interface of interface hardware 330 enables system 300 to control an operation of other devices, such as a piece of fitness equipment including corresponding network interfaces, based on a result of motion analysis.

System 300 may be configured to execute software instructions of application 350, which may include one or more software modules configured to provide various functionalities described in this disclosure. As shown in FIG. 3, application 350 includes a calibration module 352, a joints locations tracking module 354, and an output determination module 356.

Calibration module 352 can receive data of a first image (e.g., image 202 of FIG. 2A, or a set of first images) of a subject in a first posture, and then identify a set of joints from the first image based on, for example, a comparison between portions of the first image and known images of joints. The first image may be obtained by an IR camera, a TOF camera, etc., and may include depth information. After identifying the joints from the first image, calibration module 352 can determine the three-dimensional coordinates of the joints based on the depth information, as well as locations of the joints as reflected within the first image. Calibration module 352 can also determine, based on the joints locations, a set of body segments, each of which associated with a pair of joints. Calibration module 352 can also determine the locations of the set of body segments (e.g., represented by the mid-points of these body segments), and the lengths of the body segments. As discussed above, the joint locations and the body segment length information determined from the first image can be used as a reference to improve the accuracy of tracking of changes in the locations of the joints, based on which application 350 determines a body posture.

Joints locations tracking module 354 can receive data of a second image (e.g., image 242, or a set of second images) and track a motion of the joints reflected by images of the joints in the second image. Joints locations tracking module 354 can identify the joints from the second image (e.g., based on a comparison between portions of the second image and known images of joints, or a set of second images), and determine the three-dimensional coordinates of the joints from the second image. Joint location tracking module 354 can then determine a mapping relationship between the joints identified from the second image and the joints identified (by calibration module 352) from the first image, to track a motion of the joints.

As discussed above, the determination of the mapping relationship may include, for example, determining a first body segment length associated with a first pair of joints identified from the first image, and comparing the first body segment length against a second body segment length associated with a second pair of joints identified from the second image, to generate a difference. The first and second pairs of joints can be determined to represent the same pairs of joints if, for example, the difference (or a value generated based on the difference) is below a difference threshold. In some embodiments, the determination of the mapping can also be determined based on an optimization algorithm, such as sequential quadratic programming (SQP), Newton method, or other algorithms, to collectively minimize the differences of the body segment lengths associated with different pairs of joints. Based on the mapping of the joints, joints locations tracking module 354 can also track the locations and orientations of the body segments associated with the joints, and determine a body posture of the subject accordingly.

Output determination module 356 can generate additional information based on the body segments locations and orientations determined by joints location tracking module 354. The additional information to be generated can be application specific. For example, output determination module 356 may determine centers of mass locations for at least some of the body segments. A center of mass location of a body segment can be determined based on, for example, an average distribution of mass of a body segment, and the location of the body segment. As an illustrative example, if the mass density of an arm segment, on average, is uniform within the segment, output determination module 356 may determine that the centers of mass locations of the arm segment is at the mid-point of the arm segment. Accordingly, the system can determine the locations of the centers of mass.

The center of mass locations information can be used for different applications. As an illustrative example, the centers of mass locations information can be used to perform a balance assessment of a person when the person is in a certain posture in front of an image capturing device (e.g., image capturing device 102 of FIG. 1). The system may track, based on the images captured by the image capturing device, any change (and the extent of change) in the center of mass locations associated with one or more body segments of the person, to gauge the person's ability to maintain a certain posture within a certain duration of time. Based on the gauging result, the system can then perform the balance assessment. The assessment can also include other factors, such as the age of the person, a state of the surface the person is standing on (e.g., whether it is a firm surface or a soft surface), the physical condition of the person (e.g., whether the person has visual contact with the ground, etc.).

As another illustrative example, the centers of mass locations information can be used to perform a balance error scoring system (BESS) for concussion assessment, in which a person can maintain a set of static postures (e.g., double leg stance, single leg stance, tandem stance, etc.) in front of the image capturing device. The system can determine the centers of mass locations of the person from the images captured by the image capturing device, when the person is maintaining a certain posture, against a set of reference locations, to determine if there is any deviation, and the extent of deviation. The deviations may indicate the effects of head injury (if any) on static postural stability, and the system can provide a BESS assessment based on the comparison result. The assessment can also include other factors, such as the age of the person, a state of the surface the person is standing on (e.g., whether it is a firm surface or a soft surface), the physical condition of the person (e.g., whether the person has visual contact with the ground, etc.).

As another illustrative example, the center of mass locations information can also be used to perform a fall-risk assessment when the person is undergoing a motion in front of the image capturing device. For example, by tracking the change in the locations of the centers of mass (by tracking the change in the locations of the joints and the associated body segments) based on images captured by the image capturing device, the system can determine a sequence of relative movements of the body segments (e.g., the legs, the ankles, the feet, etc.) with respect to time. The system can then compare the sequence against a reference associated with a certain risk of fall. Based on the comparison result, the system can then determine a risk of fall for that person when the person undergoes that motion. The assessment can also include other factors, such as the age of the person, a state of the surface the person is standing on (e.g., whether it is a firm surface or a soft surface), the physical condition of the person (e.g., whether the person has visual contact with the ground, etc.).

Figure 4:
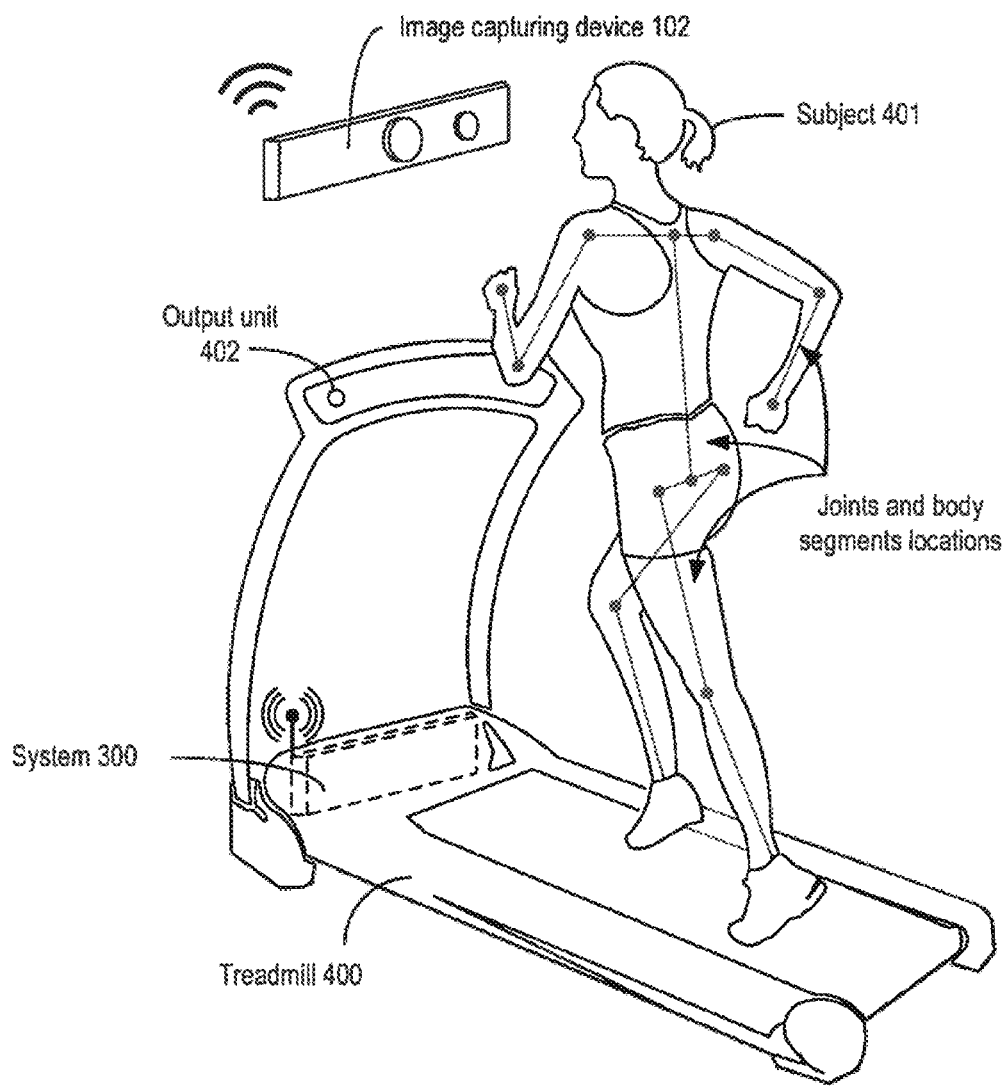
FIG. 4 is a diagram illustrating an exemplary application of a system for image-based motion analysis, consistent with embodiments of the present disclosure.

As another illustrative example, the body posture result provided by system 300 can also be used in conjunction with the operation of fitness equipment (e.g., a treadmill). Reference is now made to FIG. 4, which illustrates an application of system 300 consistent with embodiments of the present disclosure. FIG. 4 illustrates a treadmill 400 which can operate in conjunction with image capturing device 102 of FIG. 1 and system 300 of FIG. 3 (configured as motion analytics system 104 of FIG. 1). For example, image capturing device 102 captures a plurality of images of subject 401 when the subject is running on treadmill 400. Based on the image data, calibration module 352 determines the locations of a set of joints and body segments as represented by the dots and sticks, and joints location tracking module 354 track the locations of the set of joints and body segments as the subject 401 is running on treadmill 400. Output determination module 356 may also determine the probability of an event (e.g., subject 401 falling off treadmill 400) based on a state of posture of the subject 401 determined by joints location tracking module 354.

In addition to the state of posture, output determination module 356 may further determine the locations of centers of mass of subject 401 based on the locations and orientations of the body segments. For example, output determination module 356 may determine centers of mass locations for at least some of the body segments. A center of mass location of a body segment can be determined based on, for example, an average distribution of mass of a body segment, and the location of the body segment. As an illustrative example, if the mass density of an arm segment, on average, is uniform within the segment, output determination module 356 may determine that the center of mass location of the arm segment is at the mid-point of the arm segment.

After determining the center of mass locations of at least some of the body segments of subject 401, output determination module 356 can then determine the probability of an event accordingly, if such an event is related to the relative locations of the centers of mass of the subject with respect to treadmill 400. As an illustrative example, when subject 401 is running on treadmill 400, the subject may lose his or her balance (e.g., because the subject cannot keep up with the treadmill) and fall off the treadmill. The detection of subject 401 being on the verge of losing balance can be based on the posture of the subject, the location of the subject's aggregate center of mass (and/or the locations of the centers of mass of some of the user's body segments) relative to the treadmill, etc., all of which can indicate that the subject is likely to tilt (e.g. forward, backward, or sideway) and fall off the treadmill.

If output determination module 356 determines, based on the aforementioned information, that the probability of subject 401 falling off treadmill 400 exceeds a threshold, output determination module 356 can generate an indicator signal to warn subject 401. The indicator signal can include, for example, a flash light and/or a warning sound to be output by an output unit 402 on treadmill 400. Further, output determination module 356 can also transmit a signal to various components of treadmill 400 (e.g., one or more motors that control the speed and/or inclination angle of treadmill 400), to control treadmill 400 to reduce the speed and/or to reduce the inclination angle accordingly, to further reduce the probability of the user falling over the treadmill.

Although FIG. 4 provides an illustration of output determination module 356 operating in conjunction with a treadmill to improve safety, it is understood that output determination module 356 can also operate, based on the posture information determined by joints locations tracking module 354, in conjunction with other types of equipment, such as weight training equipment with adjustable weights, an elliptical, an exercise bike, a bicycle, a recumbent bike, a physical therapy device, a stepper, etc. In these cases, based on the posture information (when the user operates these other types of equipment), and based on a state of operation of these other types of equipment, output determination module 356 can determine a probability of an event that can lead to an injury (e.g., falling off the bicycle, suffering a muscle tear by the adjustable weights, etc.), and can control the equipment to mitigate the risk of injury. For example, if output determination module 356 operates in conjunction with a weight lifting machine, output determination module 356 may adjust the weights being lifted by the user, or increase an assistant force, after determining that the user is in a state of posture that can lead to injury.

In some embodiments, output determination module 356 may also provide an indication regarding information associated with the posture of the subject. Such an indication can include, for example, a notification, a warning, etc. For example, using the example above, when the user operates weight training equipment with adjustable weights, and output determination module 356 determines that the user's posture satisfies a certain criteria (e.g., overextending a muscle such that the probability of injuring that muscle increases), output determination module 356 can generate a warning (e.g., a flash light, an audio output of a warning message, etc.) to bring to the subject's attention. In some cases, output determination module 356 can also generate an indication that the subject's posture needs further evaluation, and the indication can be transmitted to an evaluator (e.g., a trainer, a physical therapist, etc.) to signal the evaluator to evaluate the posture of the subject.

In some embodiments, an indication can also be generated to signal that the subject is in a determined posture that does not need adjustment or evaluation. For example, a notification can be provided to the subject indicating that the posture is appropriate. In some embodiments, the indication can include not providing any notification to the subject when the posture of the subject is determined to be appropriate. For example, a light may flash only when the determined posture is improper, but would not flash if the determined posture is proper.

In some embodiments, output determination module 356 can also generate other application-specific information. For example, output determination module 356 can track a change of posture of the user, and determine whether the subject is exercising within a proper range of at least one of motion, posture, center of gravity, current or relative angles of body segments, etc. Output determination module 356 may also determine a training efficiency. For example, output determination module 356 can track a change of posture of the user within a period of time. Based on the change of posture, as well as the weight of the user (and/or any additional weights carried by the user), output determination module 356 can estimate an amount of calories burned by the user within that period of time, which can be used as an indicator of training efficiency. Further, output determination module 356 can also predict, based on a direction and a speed of movement of a body segment (e.g., by tracking a distance and a direction of movement by the joints within a predetermined amount of time) a predicted location and direction of the body segment, when the body segment (e.g., an arm segment) is lifting a weight. Based on the information, output determination module 356 can also determine whether the user is exercising a particular group of muscles in a certain way when lifting the weight, the determination of which can also be indicative of efficiency of the training.

Figure 5A:
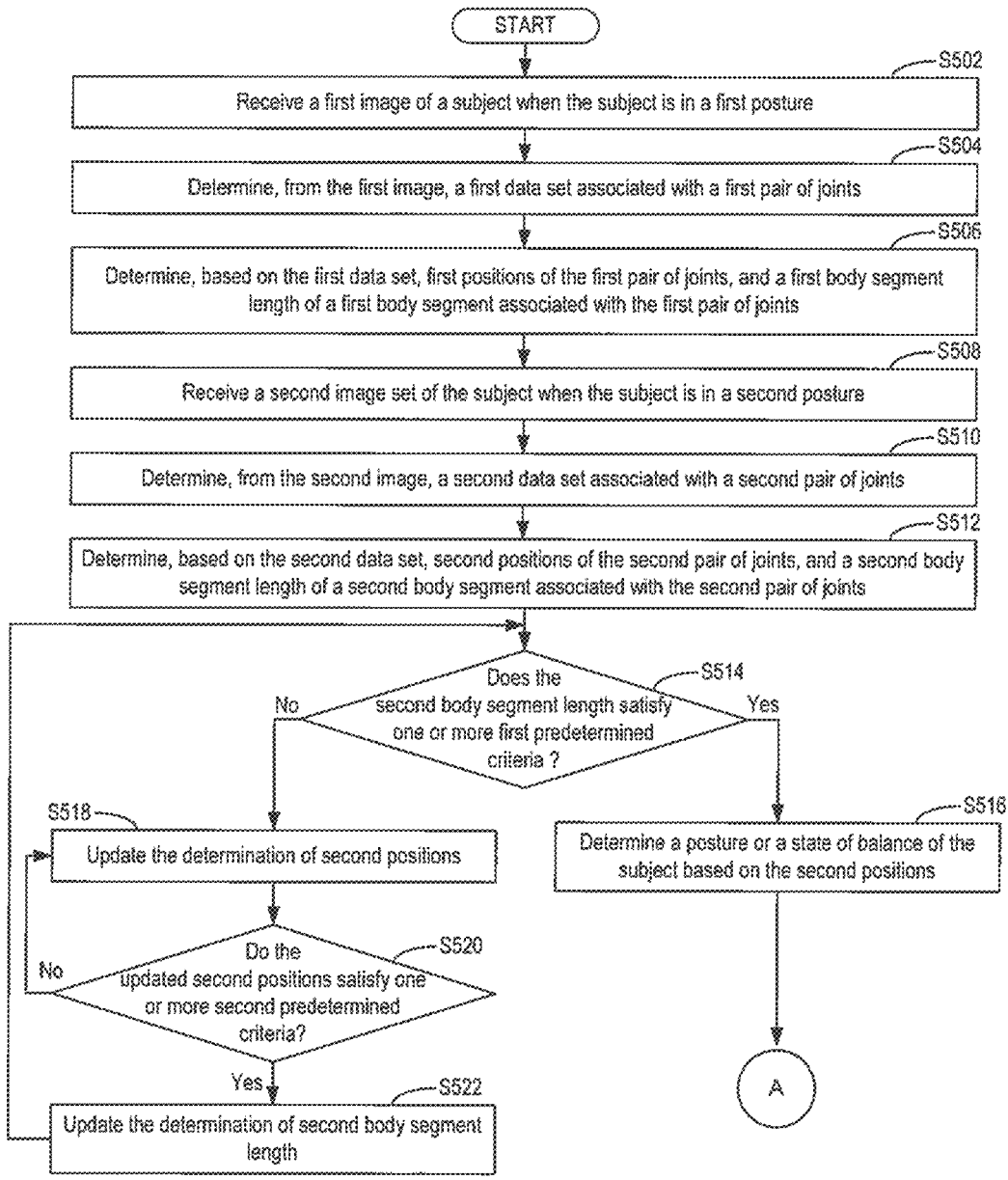
FIGS. 5A and 5B illustrate a flowchart of an exemplary method for image-based motion analysis, consistent with embodiments of the present disclosure.
Figure 5B:
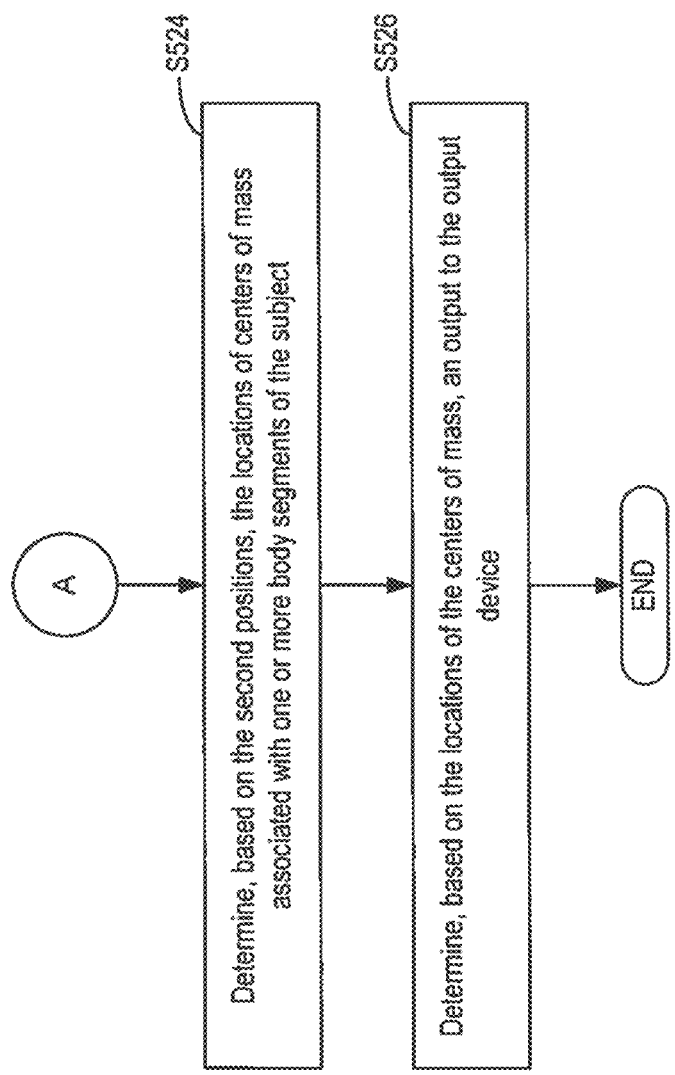

FIGS. 5A and 5B illustrate a flowchart of an exemplary method 500 consistent with the present disclosure. Method 500 may be performed by a system (e.g., system 300 of FIG. 3) that receives image data from a camera (e.g., an IR camera, a TOF camera, etc.).

After an initial start, the system receives a first image (or a set of first images) of a subject when the subject is in at least a first posture, in step S502. The first image can include an IR image, a TOF image, etc., and can include information that enables the system to determine three-dimensional coordinates of features identified from the image. For example, the first image can be an IR depth image.

The system can proceed to step S504 to determine, from the first image (or the set of first images), a first data set associated with a first pair of joints. The first data set may include data representing portions of the first image associated with the first pair of joints. The identification of the portions of the first image can be performed by, for example, comparing portions of the first image against known images of joints.

After determining the first data set in step S504, the system can proceed to step S506 to determine, based on the first data set, first positions of the first pair of joints, and a first body segment length of a first body segment associated with the first pair of joints. In some embodiments, the first image can be an IR depth image, and the first positions are represented in three-dimensional coordinates. The system can also determine, based on the first positions, a distance between the first pair of joints, and then determine, based on the distance, a first body segment length of the first body segment associated with the first pair of joints, in step S506. The system may also determine, based on the first positions of the first pair of joints, a location and an orientation of the first body segment. In some embodiments, calibration module 352 of FIG. 3 is configured to perform steps S502 to S506 of method 500.

The system can then proceed to step S508 to receive a second image (or a set of second images) of the subject when the subject is in a second posture. The system can then proceed to step S510 to determine, from the second image (or the set of second images), a second data set associated with a second pair of joints. The second data set may include data representing portions of the second image associated with the second pair of joints. The identification of the portions of the second image can be performed by, for example, comparing portions of the second image against known images of joints.

After determining the second data set, the system can then proceed to step S512 to determine, based on the second data set, second positions of the second pair of joints, and a second body segment length of a second body segment associated with the second pair of joints based on the second positions, in a similar way as the determination of the first positions of the first pair of joints and the first body segment length of the first body segment in step S506.

After determining the second body segment length in step S512, the system can then determine, based on the second body segment length, whether the first pair of joints represented in the first image and the second pair of joints represented in the second image are associated with the same pair of joints of the subject. To make such a determination, the system determines, in step S514, whether the second body segment length satisfies one or more first predetermined criteria. The first predetermined criteria may include, for example, a value related to a difference between the first and second body segments (e.g., a square of the difference, an absolute value of the difference, etc.) is below a difference threshold.

If the system determines that the second body segment length does not satisfy the one or more first predetermined criteria in step S514, the system can then proceed to step S518 to update the determination of the second positions. The updating may include, for example, identifying a different pair of joints from the second image and determining their locations as the updated second positions. The updating may also include, for example, adjusting the second positions determined in step S512 by adding an offset.

After updating a determination of the second positions in step S518, the system can then determine whether the updated second positions satisfy one or more second predetermined criteria, in step S520. The determination may include mapping a first set of joint pairs (including the first joint pairs) identified from the first image to a second set of joint pairs (including the second joint pairs) identified from the second image. The system can then determine whether the differences between the body segment lengths associated with the first set of joint pairs and the body segment lengths associated with the second set of joint pairs are minimized, for determining whether the updated second positions satisfy one or more second predetermined criteria.

In some embodiments, the determination in step S520 can be based on an optimization algorithm, such as SQP, the Newton method, etc., and can be iterative. For example, if the system determines that the updated second positions do not minimize the differences between the body segment lengths determined from the first and second images (and therefore do not satisfy the one or more second predetermined criteria), in step S520, the system can proceed back to step S518 to update the determination of the second positions (e.g., by selecting a different joint pairs, by adding a different offset, etc.). In some embodiments, the determination in step S520 can include other considerations, such as a maximum angle allowed by a joint structure. If two body segments, determined from the second image based on a set of second positions of joints, form an interior angle that exceeds the maximum angle allowed by a joint structure, the system may also discard the set of second positions and proceed back to step S518 to update the determination of the second positions.

On the other hand, if the system determines that the updated second positions satisfy the one or more second predetermined criteria (in step S520), the system can proceed to step S522 and update the second body segment length based on the updated second positions. The system can then proceed back to step S514 to determine if the updated second body segment satisfies the first predetermined criteria. In some embodiments, joints location tracking module 354 of FIG. 3 is configured to perform steps S508 to S514 of method 500.

On the other hand, if the system determines that the second body segment length satisfies the one or more first predetermined criteria in step S514, the system can then proceed to step S516 of FIG. 5B and determine a location and an orientation of the second body segment based on the second positions. The system may then proceed to step S524 to determine, based on the locations and orientations of the body segments, the locations of centers of mass associated with one or more body segments of the subject. The system may then proceed to step S526 to determine, based on the locations of the centers of mass, an output to the output device. For example, the system may perform at least one of: balance assessment, concussion assessment (e.g., based on BESS), fall-risk assessment, etc. The system may also determine that the probably of an event (e.g., a user falling off a treadmill) exceeds a threshold based on the locations of the centers of mass, and may generate a warning signal or a control signal to the treadmill according to the determination.

Computer programs created on the basis of the written description and methods of this specification are within the skill of a software developer. The various programs or program modules may be created using a variety of programming techniques. For example, program sections or program modules may be designed in or by means of Java, C, C++, assembly language, or any such programming languages. One or more of such specialized software sections or modules may be integrated into a computer system, computer-readable media, or existing communications software to perform the specialized functionality described above.

In exemplary embodiments, there is also provided a non-transitory computer readable storage medium including instructions executable by a processor for performing the above-described methods. For example, the non-transitory computer-readable storage medium may be a ROM, a RAM, a CD-ROM, a magnetic tape, a flash memory, a cache, a register, a floppy disc, an optical data storage device, and the like. The non-transitory computer-readable storage medium and the processor may be a part of a motion analytics system (e.g., motion analytics system 104 of FIG. 1). The non-transitory computer-readable storage medium and the processor can also be a part of a piece of equipment (e.g., treadmill 400 of FIG. 4). The processor can execute the instructions stored in the non-transitory computer-readable storage medium to execute, for example, method 500 of FIGS. 5A and 5B.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the methods may be modified in any manner, including by reordering steps or inserting or deleting steps. It is intended, therefore, that the specification and examples be considered as example only, with a true scope and spirit being indicated by the following claims and their full scope of equivalents.

What is claimed is:

1. A method for determining posture-related information of a subject using the subject's image, the method comprising:
   receiving a first image of a subject in a first posture;
   determining, from the first image, first positions of a first pair of joints;
   determining, from the first positions, a first body segment length of a first body segment associated with the first pair of joints;
   receiving a second image of the subject in a second posture;
   determining, from the second image, second positions of a second pair of joints;
   determining, from the second positions, a second body segment length of a second body segment associated with the second pair of joints;
   determining, based on a relationship between the first and second body segment lengths, whether the first and second pairs of joints correspond to a pair of joints of the subject;
   If the first and second pairs of joints are determined to correspond to a pair of joints of the subject, determining, based on the second positions, information of a posture of the subject; and
   providing an indication regarding the information of a posture of the subject.

2. The method of claim 1, wherein determining whether the first and second pairs of joints correspond to a pair of joints of the subject comprises: reducing a difference between the first and second body segment lengths based on an optimization algorithm.

3. The method of claim 2, wherein the optimization algorithm includes at least one of: sequential quadratic programming, and Newton method.

4. The method of claim 1, wherein determining whether the first and second pairs of joints corresponds to a pair of joints of the subject comprises:
   determining, from the second image, a third pair of joints comprising one joint of the second pair of joints;
   determining a third body segment associated with the third pair of joints; and
   determining an angle formed between the second and third body segments;
   wherein the first and second pairs of joints are determined to correspond to a pair of joints of the subject if the angle is within a threshold.

5. The method of claim 1, wherein the information of a posture of the subject comprises an estimated location of a center of mass of the subject.

6. The method of claim 5, wherein determining the information of a posture of the subject comprises: determining, based on the second image and segment densities of a plurality of body segments of the subject, the estimated center of mass of the subject.

7. The method of claim 1, wherein the indication indicates whether the subject is at risk of injury at the second posture when operating a piece of equipment.

8. The method of claim 7, wherein the piece of equipment includes one of a treadmill, a weight training equipment with adjustable weights, an elliptical, an exercise bike, a bicycle, a recumbent bike, a physical therapy device, a stepper, an exercise ball, and a multi-function exercise equipment.

9. The method of claim 1, wherein the indication indicates whether the subject maintains a posture that is in conformance with a reference posture.

10. The method of claim 9, wherein the indication indicates whether the subject has concussion.

11. A system for determining posture-related information of a subject using the subject's image, the system comprises:
a memory that stores a set of instructions; and
a hardware processor configured to execute the set of instructions to:
receive a first image of a subject in a first posture;
determine, from the first image, first positions of a first pair of joints;
determine, from the first positions, a first body segment length of a first body segment associated with the first pair of joints;
receive a second image of the subject in a second posture;
determine, from the second image, second positions of a second pair of joints;
determine, from the second positions, a second body segment length of a second body segment associated with the second pair of joints;
determine, based on a relationship between the first and second body segment lengths, whether the first and second pairs of joints correspond to a pair of joints of the subject;
If the first and second pairs of joints are determined to correspond to a pair of joints of the subject, determine, based on the second positions, information of a posture of the subject; and
provide an indication regarding information associated with the posture of the subject.

12. The system of claim 11, wherein determining whether the first and second pairs of joints correspond to a pair of joints of the subject comprises the hardware processor being configured to execute the set of instructions to: reduce a difference between the first and second body segment lengths based on an optimization algorithm.

13. The system of claim 12, wherein the optimization algorithm includes at least one of: sequential quadratic programming, and Newton method.

14. The system of claim 11, wherein determining whether the first and second pairs of joints corresponds to a pair of joints of the subject comprises the hardware processor being configured to execute the set of instructions to:
determine, from the second image, a third pair of joints comprising one joint of the second pair of joints;
determine a third body segment associated with the third pair of joints; and
determine an angle formed between the second and third body segments;
wherein the first and second pairs of joints are determined to correspond to a pair of joints of the subject if the angle is within a threshold.

15. The system of claim 11, wherein the information of a posture of the subject comprises an estimated location of a center of mass of the subject.

16. The system of claim 15, wherein determining the information of a posture of the subject comprises the hardware processor configured to execute the set of instructions to: determine, based on the second image and segment densities of a plurality of body segments of the subject, the estimated center of mass of the subject.

17. The system of claim 11, wherein the indication indicates whether the subject is at risk of injury at the second posture when operating a piece of equipment.

18. The system of claim 17, wherein the piece of equipment includes one of a treadmill, a weight training equipment with adjustable weights, an elliptical, an exercise bike, a bicycle, a recumbent bike, a physical therapy device, a stepper, an exercise ball, and a multi-function exercise equipment.

19. The system of claim 11, wherein the indication indicates whether the subject maintains a certain posture within a predetermined amount of time.

20. The system of claim 11, wherein the indication indicates whether the subject maintains a posture that is in conformance with a reference posture.

21. The system of claim 19, wherein the indication indicates whether the subject has concussion.

22. The system of claim 20, wherein the indication indicates whether the subject has concussion.

23. The system of claim 11, wherein the information of a posture of the subject comprises at least one of: a current posture, a current state of balance, and a predicted state of balance.

24. The system of claim 11, wherein determining information of a posture of the subject comprises the hardware processor configured to execute the set of instructions to: determine, based on the second positions, at least one of a location and an orientation of the second body segment.

25. The system of claim 12, wherein the difference comprises a weighted difference.

26. The system of claim 11, wherein the second image is included in a second image set that comprises two or more separate images of the subject at different times.

27. The system of claim 11, wherein at least one of the first positions and the second positions are determined based on location information of markers configured to identify at least one of body segments and joints of the subject.

28. The system of claim 11, wherein the information of a posture of the subject comprises at least one of a direction of a motion of the subject and a speed of the motion of the subject.

29. The system of claim 11, wherein the information of a posture of the subject enables a determination of a training efficiency.

30. The system of claim 11, wherein the indication indicates, when the subject is exercising, whether the subject is exercising within a proper range of at least one of motion, posture, center of gravity, current or relative angles of body segments of the subject, load, speed, static balance, dynamic balance, and time period.

31. A non-transitory computer readable medium storing instructions that are executable by one or more processors to cause the one or more processors to execute a method of determining posture-related information of a subject using the subject's image, the method comprising:
receiving a first image of a subject in a first posture;
determining, from the first image, first positions of a first pair of joints;
determining, from the first positions, a first body segment length of a first body segment associated with the first pair of joints;
receiving a second image of the subject in a second posture;
determining, from the second image, second positions of a second pair of joints;
determining, from the second positions, a second body segment length of a second body segment associated with the second pair of joints;
determining, based on a relationship between the first and second body segment lengths, whether the first and second pairs of joints correspond to a pair of joints of the subject;

If the first and second pairs of joints are determined to correspond to a pair of joints of the subject, determining, based on the second positions, information of a posture of the subject; and providing an indication regarding the information of a posture of the subject.

32. The medium of claim 31, wherein determining whether the first and second pairs of joints correspond to a pair of joints of the subject comprises the instructions executable by the one or more processors to perform: reducing a difference between the first and second body segment lengths based on an optimization algorithm.

33. The medium of claim 32, wherein the optimization algorithm includes at least one of: sequential quadratic programming, and Newton method.

34. The medium of claim 31, wherein determining whether the first and second pairs of joints corresponds to a pair of joints of the subject comprises the instructions executable by the one or more processors to perform:

determining, from the second image, a third pair of joints comprising one joint of the second pair of joints;

determining a third body segment associated with the third pair of joints; and determining an angle formed between the second and third body segments;

wherein the first and second pairs of joints are determined to correspond to a pair of joints of the subject if the angle is within a threshold.

35. The medium of claim 31, wherein the information of a posture of the subject comprises an estimated location of a center of mass of the subject.

36. The medium of claim 35, wherein determining the information of a posture of the subject comprises the instructions executable by the one or more processors to perform: determining, based on the second image and segment densities of a plurality of body segments of the subject, the estimated center of mass of the subject.

37. The medium of claim 31, wherein the indication indicates whether the subject is at risk of injury at the second posture when operating a piece of equipment.

38. The medium of claim 37, wherein the piece of equipment includes one of a treadmill, a weight training equipment with adjustable weights, an elliptical, an exercise bike, a bicycle, a recumbent bike, a physical therapy device, a stepper, an exercise ball, and a multi-function exercise equipment.

39. The medium of claim 31, wherein the indication indicates whether the subject maintains a posture that is in conformance with a reference posture.

40. The medium of claim 39, wherein the indication indicates whether the subject has concussion.

* * * * *

UNITED STATES PATENT AND TRADEMARK OFFICE
CERTIFICATE OF CORRECTION

PATENT NO. : 9,870,622 B1
APPLICATION NO. : 15/214375
DATED : January 16, 2018
INVENTOR(S) : Tung-Wu Lu et al.

Page 1 of 1

It is certified that error appears in the above-identified patent and that said Letters Patent is hereby corrected as shown below:

In the Claims

Claim 11, Column 17, Line 25, "If" should read -- if --.

Claim 31, Column 19, Line 1, "If" should read -- if --.

Signed and Sealed this
Ninth Day of October, 2018

Andrei Iancu
*Director of the United States Patent and Trademark Office*